(12) United States Patent
Guala

(10) Patent No.: US 10,926,078 B2
(45) Date of Patent: Feb. 23, 2021

(54) Y-CONNECTOR FOR MEDICAL LINES

(71) Applicant: INDUSTRIE BORLA S.p.A., Moncalieri (IT)

(72) Inventor: Gianni Guala, Turin (IT)

(73) Assignee: INDUSTRIE BORLA S.P.A, Moncalieri (IT)

(\*) Notice: Subject to any disclaimer, the term of this patent is extended or adjusted under 35 U.S.C. 154(b) by 11 days.

(21) Appl. No.: 16/327,922

(22) PCT Filed: Dec. 14, 2017

(86) PCT No.: PCT/IB2017/057944
§ 371 (c)(1),
(2) Date: Feb. 25, 2019

(87) PCT Pub. No.: WO2018/109709
PCT Pub. Date: Jun. 21, 2018

(65) Prior Publication Data
US 2019/0290897 A1    Sep. 26, 2019

(30) Foreign Application Priority Data

Dec. 15, 2016  (IT) .......................... UA2016A009078

(51) Int. Cl.
*A61M 39/26* (2006.01)
*A61M 39/04* (2006.01)
(Continued)

(52) U.S. Cl.
CPC .......... *A61M 39/26* (2013.01); *A61M 39/045* (2013.01); *A61M 39/10* (2013.01); *A61M 2039/0063* (2013.01); *A61M 2206/20* (2013.01)

(58) Field of Classification Search
None
See application file for complete search history.

(56) References Cited

U.S. PATENT DOCUMENTS

| 4,911,705 | A | * | 3/1990 | Heinzerling | .......... | A61M 39/04 |
|---|---|---|---|---|---|---|
| | | | | | | 604/86 |
| 5,533,708 | A | | 7/1996 | Atkinson et al. | | |
| | | | | (Continued) | | |

FOREIGN PATENT DOCUMENTS

| DE | 102007020859 A1 | * | 11/2008 | .......... A61M 39/045 |
|---|---|---|---|---|
| DE | 102007020859 A1 | | 11/2008 | |
| WO | 2012164514 A2 | | 12/2012 | |

OTHER PUBLICATIONS

Machine Translation of Schadt (DE 102007020859 A1). Published on Nov. 6, 2008. Translation acquired on Aug. 20, 2020. (Year: 2008).*

(Continued)

*Primary Examiner* — Jenna Zhang
(74) *Attorney, Agent, or Firm* — Heslin Rothenberg Farley & Mesiti P.C.; Victor A. Cardona, Esq.

(57) ABSTRACT

A Y-connector for medical lines, includes a tubular body provided with a first inlet coaxial to the tubular body and containing a valve device formed by an elastic element, and a second inlet arranged obliquely to the tubular body and communicating therewith between the first inlet and the outlet. The tubular body is formed with an inner septum for deviating a flow coming from the second inlet towards the hollow elastic element prior to directing the flow to the outlet.

2 Claims, 4 Drawing Sheets

(51) Int. Cl.
     *A61M 39/10*    (2006.01)
     *A61M 39/00*    (2006.01)

(56) References Cited

U.S. PATENT DOCUMENTS

| | | | |
|---|---|---|---|
| 5,782,816 A * | 7/1998 | Werschmidt | A61M 39/02 |
| | | | 604/256 |
| 2006/0027270 A1* | 2/2006 | Truitt | F16K 15/141 |
| | | | 137/843 |
| 2008/0086097 A1* | 4/2008 | Rasmussen | A61M 39/045 |
| | | | 604/266 |
| 2016/0089529 A1* | 3/2016 | Bolz | F16L 13/0209 |
| | | | 285/119 |

OTHER PUBLICATIONS

International Search Report and Written Opinion of the International Searching Authority for PCT/IB2017/057944 dated Feb. 14, 2018.

\* cited by examiner

Y-CONNECTOR FOR MEDICAL LINES

CROSS REFERENCE TO RELATED APPLICATIONS

This application is a national stage filing under section 371 of International Application No. PCT/IB2017/057944, filed on Dec. 14, 2017, published in English on Jun. 21, 2018 as WO2018/109709A1, and claims priority to Italian Application No. 102016000127162, filed on Dec. 15, 2016. The entire disclosures of each application are hereby incorporated herein by reference.

FIELD OF THE INVENTION

The present invention refers to liquid flow components for medical lines, and more in particular it regards a Y-connector typically used for introducing a secondary flow into the flow of a primary liquid.

STATE OF THE PRIOR ART

Y-connectors thus made are for example disclosed by WO-2012/164514 on behalf of the same Applicant, wherein the Y-connector comprises a tubular body having a first inlet coaxial to the tubular body and an outlet, and a second inlet arranged obliquely to the tubular body and communicating therewith between the first inlet and the outlet. The first inlet of the Y-connector is usually sealingly closed by an elastic element, conveniently hollow, having a pre-slot for introducing a secondary liquid into the primary liquid coming from the second inlet.

The first inlet can be conveniently be formed similar to a female luer lock connector, and in this case the elastic element is configured to serve as a valve: to this end, it has a hollow configuration (for example similar to the one described and illustrated in document U.S. Pat. No. 5,533,708) and axially deformable, following the coupling of the first inlet with a complementary male luer connector, between an extended closing position in which the end thereof exposed towards the external can be easily cleaned and disinfected before coupling with the male connector, and a retracted opening position.

In use, the axially extended inner cavity of the hollow elastic element can however entail a relatively large secondary liquid stagnation dead area, this being unwanted.

Document DE 102007020859 discloses a Y-connector corresponding to the preamble of claim 1. Documents US 2008/086097, US 2016/089529 and U.S. Pat. No. 4,911,705 describe similar connectors.

SUMMARY OF THE INVENTION

The object of the invention is to overcome the aforementioned technical drawback and this object is attained due to the fact that the first chamber has a radial size greater than that of the second chamber.

Thanks to this solution idea the first inlet of the Y-connector according to the invention is thus efficiently protected by the elastic element free of any risk, in use, of liquid stagnation therein, in that the liquid coming from the second inlet generates continuous replacement thereof.

The smaller radial size of the second chamber creates—in use—an advantageous effect on the dynamics of the liquid flow in the cavity of the elastic hollow element, in the area for introducing the liquid from the first inlet where greater stagnation could occur. As a matter of fact, the speed of the fluid current is greater in the second chamber with respect to that of the first chamber: thus, the pressure is lower in the second chamber with respect to that of the first chamber. This pressure difference between the two chambers translates into a vacuum in the cavity of the elastic element which, when the secondary liquid is introduced from the first inlet, facilitates the flow thereof basically suctioning it towards the second chamber, thus preventing the creation of areas for the stagnation of the secondary liquid in the cavity of the hollow element more efficiently.

Furthermore, the arrangement of the radial septum can be such to obtain a swirling flow beneath the elastic element.

BRIEF DESCRIPTION OF THE DRAWINGS

The invention will now be described in detail with reference to the attached drawings, provided purely by way of non-limiting example, wherein.

DETAILED DESCRIPTION OF THE INVENTION

Figure 1:
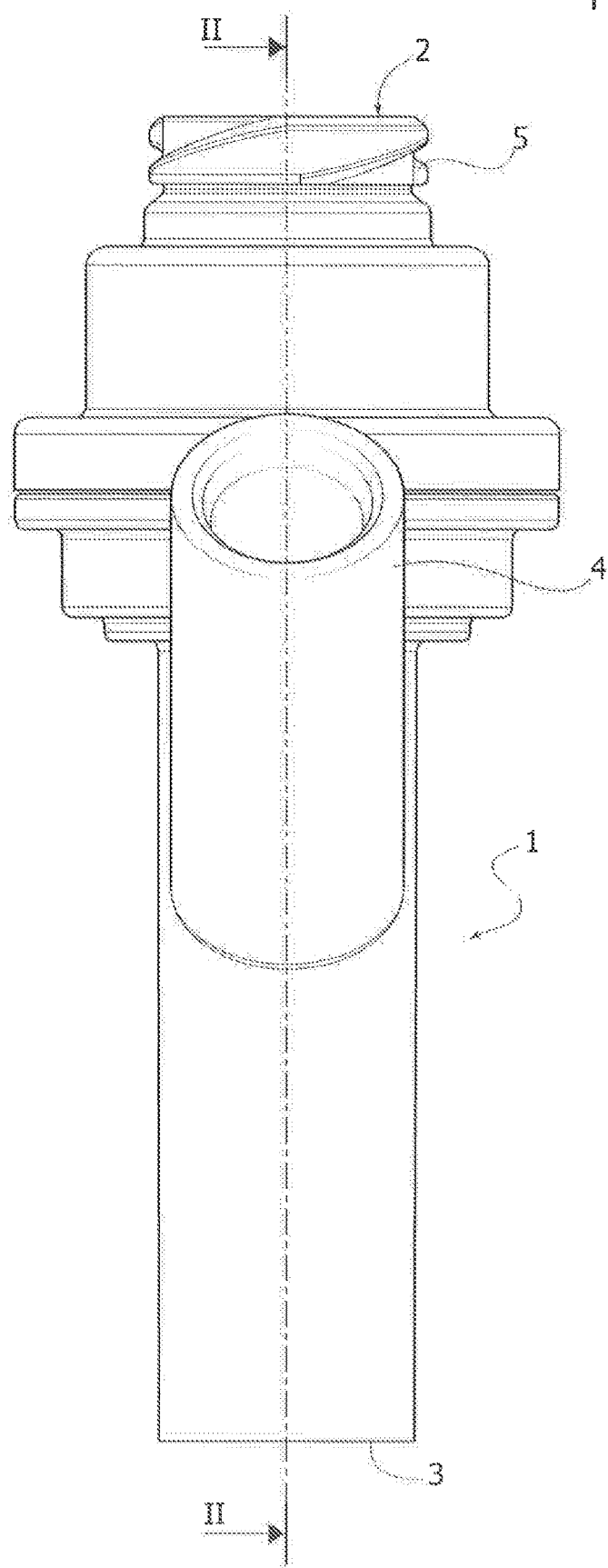
FIG. 1 is a lateral elevation schematic view of a Y-connector according to the invention.
Figure 2:
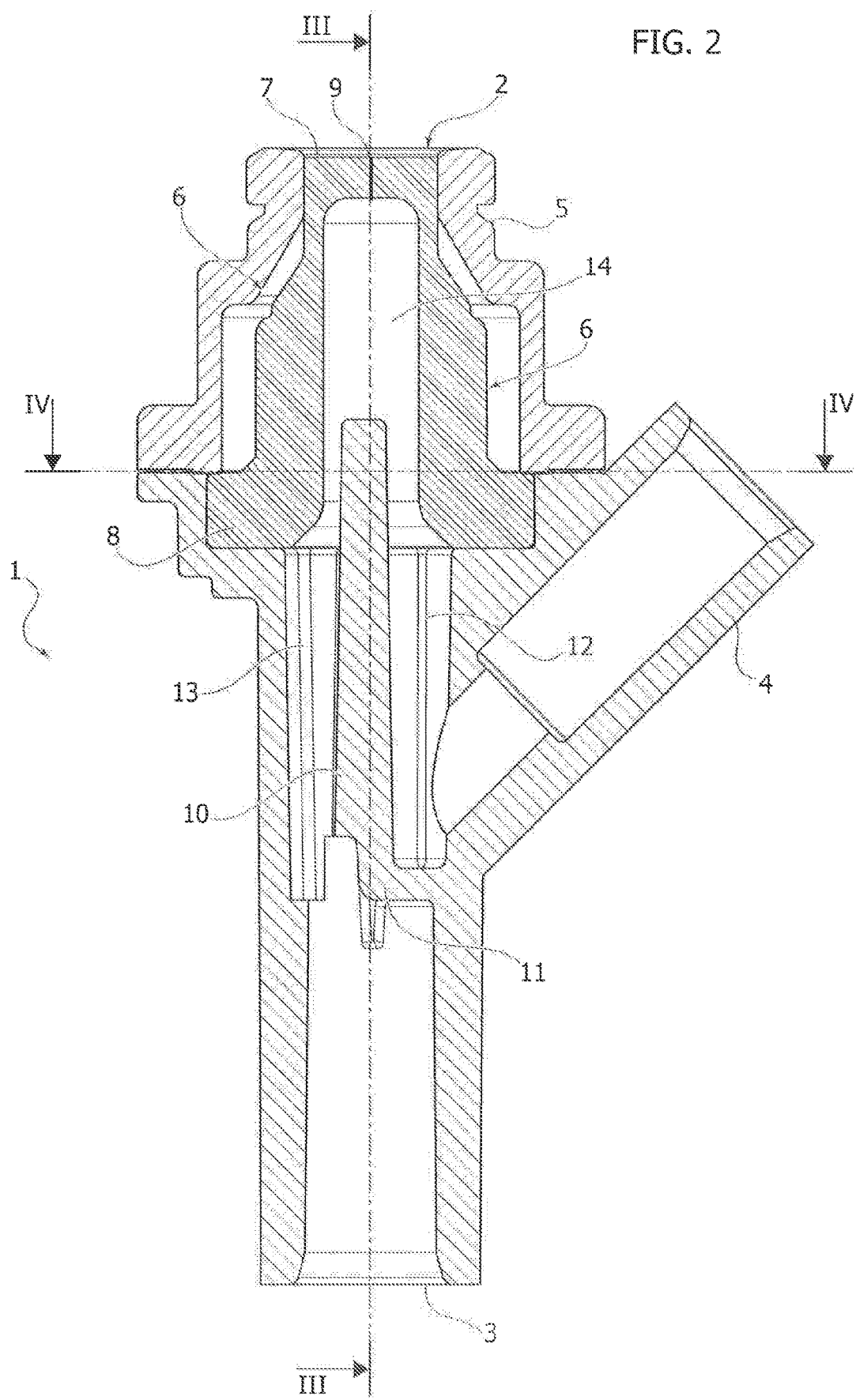
FIG. 2 is a longitudinal sectional view according to line II-II of FIG. 1.
Figure 3:
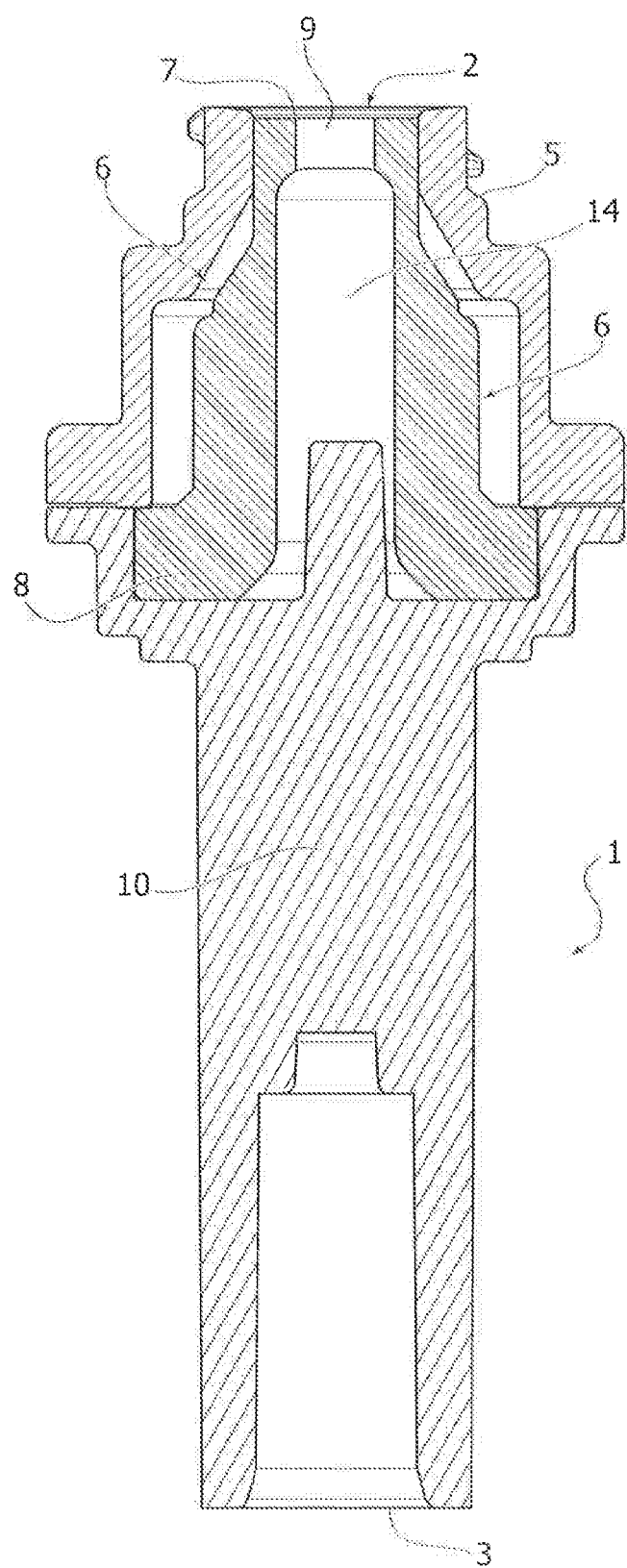
FIG. 3 is a longitudinal sectional view according to line of FIG. 2.

With reference to the drawings, the Y-connector according to the invention comprises a tubular body 1 having a first inlet 2 and an outlet 3 coaxial to the tubular body 1, and a second inlet formed by a tubular appendage 4 arranged obliquely to the tubular body 1 and communicating therewith between the first inlet 2 and the outlet 3. The second inlet 4 is designated, in use, to be connected to a medical duct of a primary liquid.

The first inlet 2 is formed similar to a female luer lock connector 5 designated to be coupled with a complementary male luer lock connector for introducing a secondary liquid, and containing a valve device formed by a hollow elastic element 6.

It should be observed that the elastic element could also be made up of a simple generally flat cachet.

The hollow elastic element 6, typically made of elastomeric material, has a distal end 7 normally arranged substantially flushed with respect to the free end of the female luer lock connector 5, and a proximal end 8 that forms a support base axially locked in the body 1. The distal end 7 is formed by a flat wall having a pre-slot 9, and it is easily cleanable and disinfectable ("swabbable").

The cavity of the hollow elastic element 6, which axially extends between the distal end 7 and the proximal end 8, is indicated with 14.

The condition represented in the drawings corresponds to the undeformed configuration of the hollow elastic element 6 wherein the first inlet 5 is sealingly closed. Should the male luer lock connector be used with the female luer lock connector 5, the hollow elastic element 6 is deformed and partly compressed ("luer activated") so as to open the pre-slot 9 and thus the communication between the first inlet 2 and the outlet 3.

According to the invention, the cavity 14 is placed in communication with the second inlet 4 in manner such that, in use, the flow of the primary liquid flowing into the tubular body 1 from such second inlet 4 penetrates into the cavity 14 of the elastic hollow element 6 prior to reaching the outlet 3, thus obtaining an action for washing the inner surface of the wall 7, beneath the pre-slot 9, thus also preventing the stagnation of the secondary liquid in the cavity 14.

To this end, the tubular body 1 is integrally obtained having an inner septum 10 for deviating the flow coming from the second inlet 4 towards the first inlet 2 and into the cavity 14 of the hollow elastic element 6. Such inner septum 10 extends axially and it is provided with a radial end portion 11 connected to the tubular body 1 in proximity of the base of the second inlet 4 to define a first chamber 12 open towards the hollow elastic element 6 and closed on the side of the outlet 3, and a second chamber 13 open towards the hollow elastic element 6 and towards the outlet 3.

Figure 4:
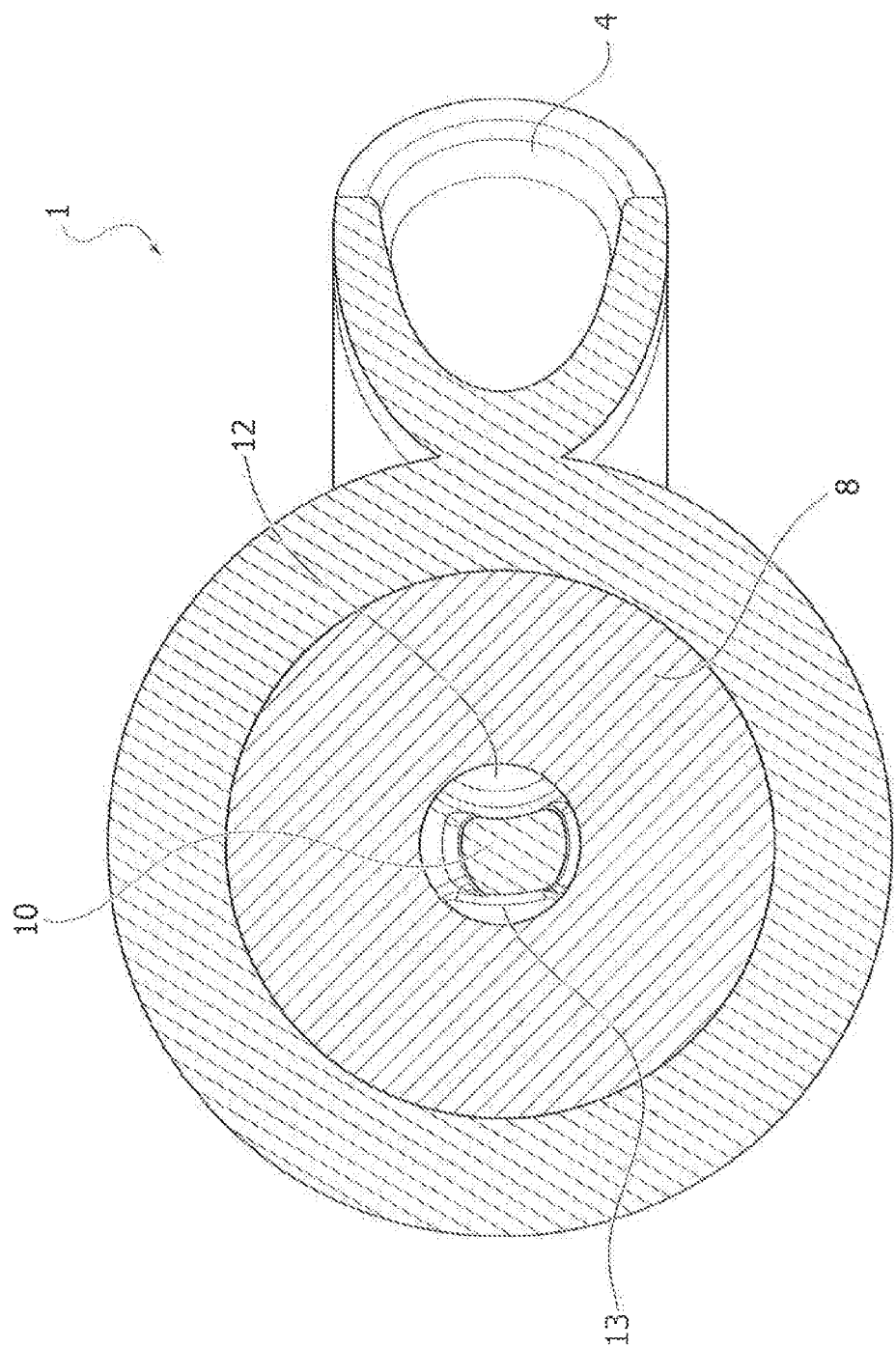
FIG. 4 is a cross-sectional view according to line Iv-Iv of FIG. 2.

The inner septum 10 is conveniently offset with respect to the axis of the tubular body 1, so that the first chamber 12 is provided with a radial size greater than that of the second chamber 13. Preferably, and as observable in FIG. 4, the inner septum 10 is offset twofold, for example in two mutually orthogonal directions as represented in FIG. 4, in a manner such that the flow coming from the second inlet 4 and deviated towards the first inlet 2 is subjected to a swirling motion, for example generally helical, which improves the effect of washing the elastic element 6 further. The surface of the inner septum 10 facing towards the first chamber 12 can be slightly concave, as equally visible in FIG. 4.

There may also be provided further deflectors, not illustrated in the drawings, configured in a manner such to accentuate the swirling motion of the liquid supplied from the second inlet 4 into the cavity 9 of the hollow elastic element 6.

Obviously, the construction details and the embodiments may widely vary with respect to what has been described and illustrated, without departing from the scope of protection of the present invention as defined in the claims that follow. Thus, as previously mentioned, the invention is equally advantageously applicable in cases where the elastic element of the Y-connector is made up of a flat cachet like in the case of the aforementioned document WO-2012/164514, instead of a hollow element. The liquid deviated from the second inlet 4 towards the first inlet 2 shall perform an efficient action for washing the inner surface of the elastic element in this case too.

The invention claimed is:

1. A Y-connector for medical lines, comprising:
 a tubular body having a first inlet coaxial with a longitudinal axis of the tubular body and containing a valve device formed by a hollow elastic element sealingly closing said first inlet in an openable manner, an outlet, and a second inlet arranged obliquely to, and extending outwardly from, a first inner surface of the tubular body and communicating therewith between said first inlet and the outlet;
 the tubular body formed with an inner septum for deviating a flow coming from the second inlet towards the elastic element prior to directing the flow to the outlet, said inner septum extending axially into an interior of the elastic element and having a radial end portion connected to the tubular body in proximity of said second inlet so as to define a first chamber open towards the elastic element and closed on an opposite side of the first chamber toward the outlet, and a second chamber open towards the elastic element and towards the outlet;
 said first chamber radially bounded by a first side of said inner septum and said first inner surface of the tubular body, said second chamber bounded by a second side of said inner septum and a second inner surface of the tubular body; and
 wherein a longitudinal axis of said inner septum is offset relative to the longitudinal axis of the tubular body such that the first chamber has a radial size greater than that of the second chamber;
 wherein said inner septum is provided with a concave surface facing towards said first chamber.

2. Y-connector according to claim 1, wherein said inner septum is offset twofold with respect to the longitudinal axis of the tubular body in mutually orthogonal directions in such a manner that the flow coming from the second inlet is deviated towards the first inlet with a swirling motion.

* * * * *

UNITED STATES PATENT AND TRADEMARK OFFICE
CERTIFICATE OF CORRECTION

PATENT NO. : 10,926,078 B2
APPLICATION NO. : 16/327922
DATED : February 23, 2021
INVENTOR(S) : Gianni Guala Page 1 of 1

It is certified that error appears in the above-identified patent and that said Letters Patent is hereby corrected as shown below:

On the Title Page

Foreign Application Priority Data Item (30):
Delete "UA2016A009078" and insert -- 102016000127162 --

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*